(12) United States Patent
Dabney

(10) Patent No.: US 10,016,456 B2
(45) Date of Patent: Jul. 10, 2018

(54) METHODS FOR TREATING ACNE VULGARIS

(71) Applicant: Paul Dabney, Georgetown, TX (US)

(72) Inventor: Paul Dabney, Georgetown, TX (US)

(73) Assignee: DABNEY PATENTS, L.L.C., Georgetown, TX (US)

( * ) Notice: Subject to any disclaimer, the term of this patent is extended or adjusted under 35 U.S.C. 154(b) by 462 days.

(21) Appl. No.: 14/638,902

(22) Filed: Mar. 4, 2015

(65) Prior Publication Data

US 2016/0015744 A1 Jan. 21, 2016

Related U.S. Application Data

(63) Continuation-in-part of application No. 14/497,269, filed on Sep. 25, 2014, now Pat. No. 9,579,177, and a continuation-in-part of application No. 14/536,633, filed on Nov. 9, 2014, now Pat. No. 9,504,848, and a continuation-in-part of application No. 14/583,580, filed on Dec. 26, 2014, and a continuation-in-part of application No. 14/630,513, filed on Feb. 24, 2015, now Pat. No. 9,700,735.

(60) Provisional application No. 62/026,498, filed on Jul. 18, 2014.

(51) Int. Cl.
| | | |
|---|---|---|
| *A61K 33/22* | (2006.01) | |
| *A61K 9/00* | (2006.01) | |
| *A61K 33/40* | (2006.01) | |
| *A61K 31/327* | (2006.01) | |
| *A61K 9/08* | (2006.01) | |
| *A61K 31/465* | (2006.01) | |
| *A61K 31/60* | (2006.01) | |
| *A61K 33/04* | (2006.01) | |
| *A61K 31/192* | (2006.01) | |
| *A61K 31/19* | (2006.01) | |
| *A61K 9/06* | (2006.01) | |

(52) U.S. Cl.
CPC .......... *A61K 33/40* (2013.01); *A61K 9/0014* (2013.01); *A61K 9/06* (2013.01); *A61K 9/08* (2013.01); *A61K 31/19* (2013.01); *A61K 31/192* (2013.01); *A61K 31/327* (2013.01); *A61K 31/465* (2013.01); *A61K 31/60* (2013.01); *A61K 33/04* (2013.01); *A61K 33/22* (2013.01)

(58) Field of Classification Search
CPC ........ A61K 33/40; A61K 9/06; A61K 9/0014; A61K 9/08; A61K 31/19; A61K 31/192
See application file for complete search history.

(56) References Cited

U.S. PATENT DOCUMENTS

| | | | | |
|---|---|---|---|---|
| 4,292,971 A | * | 10/1981 | Smit | .......................... A61F 7/02 604/23 |
| 8,632,822 B2 | * | 1/2014 | Piergallini | ........... A61K 31/352 424/616 |
| 2007/0244195 A1 | * | 10/2007 | Burkhart | ................ A61K 31/13 514/568 |
| 2016/0175324 A1 | * | 6/2016 | Dayan | .................... A61K 31/00 514/182 |

OTHER PUBLICATIONS

Reddi, Benjamin, "Why is Saline so Acidic (and Does It Really Matter?)" International Journal of Medical Sciences, 2013; 10(6) 747-750, Apr. 2013. https://www.ncbi.nlm.nih.gov/pmc/articles/PMC3638298/.*

* cited by examiner

Primary Examiner — Leslie Deak
Assistant Examiner — Gabriella Burnette
(74) Attorney, Agent, or Firm — Maier & Maier, PLLC

(57) ABSTRACT

Methods for treating acne vulgaris include providing a solution having a peroxide compound, the solution having an antimicrobial effect for reducing bacteria that cause acne vulgaris; topically administering a therapeutically effective amount of the solution to the patient; and once administered, exposing the solution to a wavelength of light that creates a synergistic antimicrobial effect with the solution and enhances the antimicrobial effect of the solution, thereby further reducing or eliminating the bacteria that cause acne vulgaris. The methods may decrease lesions and associated inflammation in patients infected with acne vulgaris.

24 Claims, No Drawings

METHODS FOR TREATING ACNE VULGARIS

RELATED APPLICATIONS

This application claims the benefit of the filing date of U.S. Patent Application No. 62/026,498, filed Jul. 18, 2014, which is incorporated herein by reference in its entirety, U.S. patent application Ser. No. 14/497,269, filed Sep. 24, 2014, which is incorporated herein by reference in its entirety; U.S. patent application Ser. No. 14/536,633, filed Nov. 9, 2014, which is incorporated herein by reference in its entirety; U.S. patent application Ser. No. 14/583,580, filed Dec. 26, 2014, which is incorporated herein by reference in its entirety, and U.S. patent application Ser. No. 14/630,513, filed Feb. 24, 2015, which is incorporated herein by reference in its entirety.

BACKGROUND OF THE INVENTION

The present invention generally relates to medical therapy, and more specifically for methods for treating acne vulgaris.

Acne vulgaris is an inflammatory disease of the pilosebaceous glands characterized by an eruption of the skin, often pustular in nature but not suppurative. One common bacteria associated with this disease is propionibacterium acnes. Acne is a common affliction of the adolescent and affects a small but significant percentage of the adult population. Acne lesions are of four basic types: comedones (blackheads or whiteheads), papules, pustules, and cysts (or nodules). Acne inflammatory disease results in unsightly lesions, particularly on the face, and in some cases results in severe scarring. Microbes, including or related to acne, exist that cause harm or disease in living tissues of humans and animals.

It would be desirable to add light of certain wavelengths to solutions for treatment of patients having acne vulgaris.

SUMMARY OF THE INVENTION

In an aspect of the present invention, a method of decreasing lesions and associated inflammation in patients infected with acne vulgaris includes providing a solution having a peroxide compound, the solution having an antimicrobial effect for reducing bacteria that cause acne vulgaris; topically administering a therapeutically effective amount of the solution to the patient; and once administered, exposing the solution to a wavelength of light that creates a synergistic antimicrobial effect with the solution and enhances the antimicrobial effect of the solution, thereby further reducing or eliminating the bacteria that cause acne vulgaris.

DETAILED DESCRIPTION

This application does not include any drawings. The primary embodiments can be described utilizing words alone.

The preferred embodiment and other embodiments, which can be used in industry and include the best mode now known of carrying out the invention, are hereby described in detail. Further embodiments, features and advantages will become apparent from the ensuing description, or may be learned without undue experimentation. The following description of embodiments, even if phrased in terms of "the invention" or what the embodiment "is," is not to be taken in a limiting sense, but describes the manner and process of making and using the invention. The coverage of this patent will be described in the claims. The order in which steps are listed in the claims does not necessarily indicate that the steps must be performed in that order. The phrase "and/or" between two elements means the first element alone, the second element alone, or both elements together.

An embodiment of the present invention generally provides medical and application of light combined with a peroxide and possibly also further acne-related chemicals for the treatment of acne.

Light of certain wavelengths has been demonstrated to improve or "super-charge" the effects of certain pharmaceuticals such as antimicrobial or other acne-therapeutic agents, creating a synergistic effect to destroy or inhibit microbial or anti-acne growth.

Embodiments of an antimicrobial solution or other acne-related chemical may reduce the bacterial count of acne causing organisms. The antimicrobial solution when exposed to certain wavelength of light may create a synergistic effect that causes a greater reduction in the bacterial count. This increased effectiveness may allow for a greater reduction in the bacterial count and/or a reduction in the needed strengths of the chemical making up the antimicrobial solution, and/or a shorter time needed with the solution in contact with the patient's tissues.

Embodiments of a method of treating acne vulgaris ("acne") may include administering a therapeutically effective amount of a peroxide solution with light of a certain wavelength range that may be used in combination with one or more other antimicrobials or other chemicals that may consist of topical antibiotic, topical anesthetic, nicotinic acid, nicotinamide, antimicrobials such as clindamycin phosphate, Methyl 7-chloro-6,7,8-trideoxy-6-(1-methyl-trans-4-propyl-L-2-pyrrolidinecarboxamido)-1-thio-L-threo-α-D-galacto-octopyranoside 2-(dihydrogen phosphate). Embodiments of an antimicrobial may include salicylic acid, sulfur, retinoids such as 6-[3-(1-adamantyl)-4-methoxy-phenyl]naphthalene-2-carboxylic acid, glycolic acid, tretinoin, borax, and additional chemicals useful in said method. Embodiments of topical and systemic agents may be utilized as therapeutic chemicals in embodiments of the present invention for the treatment of acne, including hydrogen peroxide, carbamide peroxide, sulfur, retinoids such as 6-[3-(1-adamantyl)-4-methoxy-phenyl]naphthalene-2-carboxylic acid, glycolic acid, borax, resorcinol, salicylic acid, benzoyl peroxide, vitamin A acid (tretinoin) and topical and systemic antibiotics. Embodiments including combinations of various peroxide compounds with certain chemical agents may be effective in treating acne, and have a synergistic effect in treating acne that is greater than the effect expected by treatment with the individual agents themselves. This synergistic effect has an even greater synergistic effect when exposed to certain wavelengths of light. The second chemical may be a therapeutic chemical or acne-therapeutic chemical because it contains elements which are helpful in reducing acne and are used in an acne treatment or acne-related therapy.

As an example, research has shown that embodiments with hydrogen peroxide may kill 30% of bacteria that are exposed to it for 20 seconds. Light of the wavelength 360 nM-500 nM may kill 3% of bacteria that are exposed to it for 20 seconds. Hydrogen peroxide in combination with light of 360 nM-500 nM may exhibit a synergistic reaction that kills 96% of bacteria exposed to this combination for 20 seconds. Formulations of the solutions used in embodiments of this invention may include combinations of hydrogen peroxide and/or carbamide peroxide and/or benzoyl peroxide and one or more of sulfur, retinoids such as 6-[3-(1-adamantyl)-4-methoxy-phenyl]naphthalene-2-carboxylic acid, glycolic acid, borax, resorcinol, salicylic acid, vitamin A acid (tretinoin) and topical and systemic antibiotics.

Acne inflammatory disease results in unsightly lesions, particularly on the face, and in some cases results in severe scarring. This invention may decrease the inflammatory disease and the associated scarring by creating a synergistic antimicrobial effect between an antimicrobial solution and a light of certain predetermined wavelengths. The resulting synergistic effect is greater than the effect of the antimicrobial solution or the light acting alone.

In an embodiment of this invention, topical solutions of hydrogen peroxide and/or carbamide peroxide and/or benzoyl peroxide and other chemicals deemed effective may be delivered in various organic vehicles or carriers. Embodiments of carriers may include a combination of ethyl alcohol and propylene glycol in which the active ingredient may present in the range of from about 0.001% to about 50% by volume of the carrier. The pH of the solution may be adjusted so that tissue sensitivity is minimized while the effectiveness of the solution is not hampered. The temperature of the solution may be adjusted to optimize its effectiveness.

For safety and for optimizing effectiveness of the solution, a "scalding chart" might be provided or used. This chart may indicate that water of 130 degrees is safe under an exposure of 30 seconds, but over that it causes burns. Water of 120 10 degrees may be safe up to 5 minutes. Solutions warmer than normal body temperature will tend to open pores exposing bacteria to greater amounts of the solution. Systemic antimicrobial agents may be used as a part of an embodiment of this treatment to increase its effectiveness. The solution may be exposed to light in a wavelength of 360 nM-600 nM or any other wavelength that proves effective for a certain time that may range from 1 second to 1 minute. Embodiments may include a solution that may be warmed, and light creates the synergistic effect that is unique to this invention. This light may be used in varying distances from the solution to modulate its synergistic effect.

In an additional embodiment, topical solutions of peroxide compounds may include hydrogen peroxide and/or carbamide peroxide and/or benzoyl peroxide in various organic carriers in concentrations that may range from 0.001 to 50% by volume of the carrier. In embodiments, the compounds may be incorporated into various vehicles or carriers including solutions, lotions, creams, gels, mists, pastes and ointments along with one or more of the following ingredients: nicotinic acid or nicotinamide that may be present in concentrations from 0.001% to 30% by volume of the carrier; erythromycin base in concentrations that may present from 0.001% to about 30% by volume of the carrier; clindamycin phosphateMethyl 7-chloro-6,7,8-trideoxy-6-(1-methyl-trans-4-propyl-L-2-pyrrolidinecarboxamido)-1-thio-L-threo-α-D-galacto-octopyranoside 2-(dihydrogen phosphate). Embodiments may have concentrations of from 0.001 to 30% by volume; tetracycline hydrochloride in concentrations of from 0.001 to 30% by volume of the carrier; retinoids such as 6-[3-(1-adamantyl)-4-methoxy-phenyl]naphthalene-2-carboxylic acid; and other ingredients deemed effective in treating acne vulgaris. In embodiments, such carriers may be useful for the incorporation of carbamide peroxide and may include combinations of ethyl alcohol and propylene glycol, surface active agents such as lauryl ethers and lauryl esters, and other carriers effective for this invention. Applications of the carrier and effective ingredients may be made to the face or other infected areas of acne patients. This treatment may be applied at varying intervals such as 1 to 4 times in a 24 hour period with the result that open and closed comedones (blackheads and whiteheads), and inflamed lesions are greatly reduced within a period of days to weeks varying with the number of applications per day.

Embodiments of the present invention may provide an improved method for the treatment of acne vulgaris involving the periodic application of an antimicrobial solution containing an effective amount of peroxide agents alone or in combination with one or more of a topical antibiotic, topical anesthetic, nicotinic acid, nicotinamide, antimicrobials, salicylic acid, sulfur, retinoids such as 6-[3-(1-adamantyl)-4-methoxy-phenyl]naphthalene-2-carboxylic acid, glycolic acid, tretinoin, borax, and additional chemicals useful in said method. This antimicrobial solution may be applied to patients with the inflammatory disease, acne vulgaris. The antimicrobial solution may be adjusted to a temperature that is optimal for this treatment. The antimicrobial solution may be applied over the acne vulgaris lesions and associated inflamed tissue. Once applied, the antimicrobial solution may be exposed to a wavelength of light that creates a synergistic effect enhancing the effectiveness of the antimicrobial solution. This synergistic effect may cause a greater reduction in bacteria associated with acne vulgaris than the applications of the antimicrobial solution alone or the light alone.

Embodiments of a solution may contain a light activated pigment that may fluoresce when exposed to the wavelength of light used in the treatment. This pigment could indicate to the user that the synergistic effect is occurring.

The following specific examples help illustrate the present invention, which is not limited to the examples.

EXAMPLE 1

In one embodiment, a 3% solution of hydrogen peroxide in a gel carrier is prepared. Twice daily topical applications of this solution are administered to an infected area on a patient suffering from acne vulgaris. After application, the solution is exposed to a 360-500 nM wavelength of light for 20 seconds creating a synergistic effect that is greater than the application of the light or the solution alone. This light is applied by a LED device the exposes the patients entire infected area at one time. The solution is then rinsed off with clean water. After two weeks of treatment, the comedone count on the patient, and the inflamed areas that result from an acne infection will have measurably declined. This synergistic effect between the solution and the light is unique to this invention.

EXAMPLE 2

In another embodiment, a solution of containing 3% hydrogen peroxide, 3% benzoyl peroxide, and salicylic acid are combined in a carrier in cream form. This solution is buffered to a pH of 6. This cream is applied to areas infected with acne vulgaris on a patient one time per daily. Once the cream is applied, it is exposed to a 10 watt, hand help light emitting light in wave lengths from 410 nM-500 nM thus creating a synergistic effect between the solution and the light causing a greater reduction in microbes then the light or the solution acting alone. The light may have a termination that radiates this light that is 15 mm in diameter. This particular size would enable the patient to target small areas. The exposure time of the light is one minute. This embodiment of the invention may be used to maintain an area that once exhibited an active acne vulgaris infection. This synergistic relationship between the light and the solution is unique to this invention.

EXAMPLE 3

In yet another embodiment, a solution containing 15% carbamide peroxide, 2.5% clindamycin phosphateMethyl 7-chloro-6,7,8-trideoxy-6-(1-methyl-trans-4-propyl-L-2-pyrrolidinecarboxamido)-1-thio-L-threo-α-D-galacto-octopyranoside 2-(dihydrogen phosphate). Embodiments may include tretinoin are combined in a gel form carrier This carrier solution is heated to 105 degrees Fahrenheit. The warmed solution helps to open the patient's pores once it is applied to the infected area. This solution is applied three times per day. The infected area is exposed to a light of 410 nM-500 nM by a lamp that would expose an area with a diameter of 30 centimeters. The infected area and solution are exposed to this certain wavelength of light for 30 seconds. The synergistic effect of the light and solution that may be warmed is greater than the effect of the light or the solution acting individually. This synergistic effect between the light and the solution that may be warmed is unique to this invention.

Embodiments may include a method of decreasing open and closed comedones and associated inflammation in patients infected with acne vulgaris by topically administering a therapeutically effective amount of peroxide compounds and other therapeutic chemicals that together form a solution that is an effective antimicrobial compound for treating acne vulgaris. This solution, once applied, is exposed to a wavelength of light that creates a synergistic antimicrobial effect that reduces or eliminates bacteria causing acne vulgaris. This synergistic antimicrobial effect is greater than the solution's antimicrobial effect or the light's antimicrobial effect if they were used separately.

I claim:

1. A method of decreasing lesions and associated inflammation in patients infected with acne vulgaris, comprising:
   providing a solution having a peroxide compound, the solution having an antimicrobial effect for reducing bacteria that cause acne vulgaris;
   heating the solution to a temperature in a range of 99° F. to 120° F. in order to optimize its effectiveness;
   topically administering a therapeutically effective amount of the heated solution to the patient; and
   once administered, exposing the heated solution to a wavelength in a range of 360 nM to 500 nM of light that creates a synergistic antimicrobial effect with the heated solution and enhances the antimicrobial effect of the heated solution, thereby further reducing or eliminating the bacteria that cause acne vulgaris.

2. The method of claim 1, wherein said peroxide compound is dispersed in a pharmaceutically acceptable carrier.

3. The method of claim 2, wherein the carrier is a gel, mist, lotion, cream, liquid, paste, or powder.

4. The method of claim 2, wherein the carrier is a gel.

5. The method of claim 2, wherein the carrier is a mist.

6. The method of claim 2, wherein the carrier is a cream.

7. The method of claim 2, wherein the carrier is a liquid.

8. The method of claim 2, wherein the carrier is a paste.

9. The method of claim 2, wherein the carrier is a powder.

10. The method of claim 1, wherein said peroxide compound is dispersed in a pharmaceutically acceptable carrier and the peroxide compound is present in the amount of not less than 0.001% by volume of the carrier a less than 50% by volume of the carrier.

11. The method of claim 1, wherein the solution further includes a light activated pigment that fluoresces when exposed to the wavelength of light.

12. The method of claim 1, wherein the solution further includes at least one therapeutic chemical so that the peroxide compound and therapeutic chemical together form a solution that is an effective antimicrobial compound for treating acne vulgaris.

13. The method of claim 12, wherein the therapeutic chemical includes one or more of: a topical antibiotic, topical anesthetic, nicotinic acid, nicotinamide, antimicrobials, salicylic acid, sulfur, retinoids such as 6-[3-(1-adamantyl)-4-methoxy-phenyl]naphthalene-2-carboxylic acid, glycolic acid, tretinoin, or borax, and the light creates a synergistic effect that enhances the effectiveness of the therapeutic chemical in treating acne vulgaris.

14. The method of claim 12, wherein the therapeutic chemical includes a topical antibiotic.

15. The method of claim 12, wherein the therapeutic chemical includes a topical anesthetic.

16. The method of claim 12, wherein the therapeutic chemical includes nicotinic acid or nicotinamide.

17. The method of claim 12, wherein the therapeutic chemical includes a second antimicrobial chemical having a second antimicrobial effect.

18. The method of claim 12, wherein the therapeutic chemical includes salicylic acid.

19. The method of claim 12, wherein the therapeutic chemical includes sulfur.

20. The method of claim 12, wherein the therapeutic chemical includes a retinoid.

21. The method of claim 12, wherein the therapeutic chemical includes 6-[3-(1-adamantyl)-4-methoxy-phenyl]naphthalene-2-carboxylic acid.

22. The method of claim 12, wherein the therapeutic chemical includes glycolic acid.

23. The method of claim 12, wherein the therapeutic chemical includes tretinoin.

24. The method of claim 12, wherein the therapeutic chemical includes borax.

* * * * *